United States Patent [19]

Suto

[11] Patent Number: 5,064,576

[45] Date of Patent: Nov. 12, 1991

[54] STEAM SENSITIVE COMPOSITION AND A STERILIZATION INDICATOR COMPOSITION CONTAINING THE SAME

[75] Inventor: Kyoko Suto, Sagamihara, Japan

[73] Assignee: Minnesota Mining and Manufacturing Company, St. Paul, Minn.

[21] Appl. No.: 397,046

[22] Filed: Aug. 22, 1989

[30] Foreign Application Priority Data

Aug. 26, 1988 [JP]  Japan .................................. 63-212305

[51] Int. Cl.$^5$ ............................................. C07F 15/04
[52] U.S. Cl. ......................................... 252/962; 556/37
[58] Field of Search .......................... 252/962; 556/37; 549/206

[56] References Cited

U.S. PATENT DOCUMENTS

| | | | |
|---|---|---|---|
| 2,118,144 | 8/1932 | Bekman et al. | 252/962 |
| 2,886,591 | 5/1954 | Lautenschlager | 556/37 |
| 2,889,779 | 1/1955 | Korpman | 116/114 |
| 3,360,337 | 12/1967 | Edenbaum | 2/253 |
| 3,386,807 | 6/1968 | Edenbaum | 23/253 |
| 3,512,999 | 5/1970 | Dimroth | 556/37 |
| 3,667,916 | 6/1972 | Silva et al. | 23/230 R |
| 4,240,926 | 12/1980 | McNeely | 252/408 |
| 4,240,981 | 12/1980 | Kok | 556/37 |
| 4,248,837 | 2/1981 | Lai et al. | 556/37 |
| 4,301,223 | 11/1981 | Nakamura et al. | 556/37 |
| 4,620,941 | 11/1986 | Yoshikawa et al. | 252/408.1 |
| 4,743,398 | 5/1988 | Brown et al. | 252/962 |

FOREIGN PATENT DOCUMENTS

| | | |
|---|---|---|
| 0282178 | 2/1988 | European Pat. Off. . |
| 0353189 | 7/1989 | European Pat. Off. . |
| 454690 | 12/1965 | Japan . |
| 5913550 | 11/1976 | Japan . |
| 2179050 | 2/1987 | United Kingdom .................. 556/37 |

OTHER PUBLICATIONS

Kirk-Othmer, "Encyclopedia of Chemical Technology", 2nd Edition, vol. 13, pp. 735-765 (1967).
Bloomquist et al., "Thermochromic Phase Transistions in Transion Metal Salts", coordination Chemistry Reviews, 47, pp. 125-164 (1982).
Patent Abstract JP-B-45-4690 (English Translation).
Patent Abstract JP-B-59-13550 (English Translation).
Patent Abstract JP-B-55-18464 (English Translation).
Patent Abstract JP-A-51-3381 (English Translation).
"Metal Complexes of Furfurylamine Derivatives", by M. D. Joestein, K. C. Claus, and K. P. Lannert, Dept. of Chem. South Illinois University, J. Inorganic Nuclear Chem. 1967, vol. 29, pp. 1421 to 1426.
Study of Ligand Isomeric Complexes of N-Furfurylsalicylaldimine, by U. A. Bhagwat, V. A. Mukhedkar, and A. J. Mukhedkar, Dept. of Chem. the University of Poona 411007 India, Feb. 1979.

Primary Examiner—Robert L. Stoll
Assistant Examiner—Joseph D. Anthony
Attorney, Agent, or Firm—Gary L. Griswold; Walter N. Kirn; Jennie G. Boeder

[57] ABSTRACT

A steam sensitive composition and a sterilization indicator composition which change in color only upon exposure to all of the conditions necessary for sterilization, that is, steam at a prescribed temperature for a prescribed period of time. The steam sensitive composition contains a metal complex and an exchange ligand. The metal complex is bis(dimethylglyoximato)nickel, bis(2-furyldioximato)nickel, zirconium chloranilate or bis(nioximato)nickel; and the exchange ligand is either 1) an aminocarboxylic acid which comprises from 1 to 6 carboxylic acid groups and from 1 to 4 amino groups, and its salts; or 2) citric or tartaric acids and their salts. The sterilization indicator contains as main components the steam sensitive composition described above, a binder, a solvent and preferably a color-change rate regulating component. The rate regulating components may be a cyanate or thiocyanate salt, and/or tartaric or citrate acid or their salts.

12 Claims, No Drawings

STEAM SENSITIVE COMPOSITION AND A STERILIZATION INDICATOR COMPOSITION CONTAINING THE SAME

BACKGROUND OF THE INVENTION

1. Field of the Invention

The present invention relates to a steam sensitive composition and a sterilization indicator composition which markedly change in color upon exposure to steam sterilization treatment. More particularly, the present invention relates to a steam sensitive composition and a sterilization indicator composition which may be incorporated in steam sensitive paints or inks used in the packaging of medical instruments, retort foods, etc., and other steam sterilizable articles. These steam sensitive paints or inks change color upon exposure to a steam sterilization process of a prescribed temperature for a prescribed period of time.

2. Background

Steam sensitive compositions and sterilization indicator compositions which contain as main components a metal compound, such as lead carbonate, and sulfur, have so far generally been used. U.S. Pat. No. 2,889,799 disclosed such compositions. Such sterilization marking inks are disclosed in JP-B-45-4690. Further, heat sensitive compositions utilizing a color change at the time of formation or decomposition of metal complexes are disclosed in JP-A-51-3381. Further, examples of the application of steam sensitive compositions to inks are disclosed in JP-B-55-18464 and JP-B-59-13550.

However, the conventional steam sensitive compositions and sterilization indicator compositions are not always satisfactory for one or more of the following reasons:

1) Color development is limited to black or other dark colors.
2) Since color change begins as soon as a definite temperature is reached, it is impossible to confirm whether or not treatment with steam and for the period of time essential to accomplish sterilization has been completed.
3) The components of the compositions are sublimable, so that the storage stability is poor and color change may not occur uniformly.
4) There is an offensive odor, particularly with compositions containing sulfur.

Particularly, those which utilize the formation reaction of metal complexes easily change in color with heat alone, so that it is difficult to confirm whether or not steam is present for the necessary period of time. Both those which utilize the formation reaction of metal complexes and those which utilize the decomposition reaction of metal complexes are lacking in storage stability. Particularly those which utilize the decomposition reaction of metal complexes exhibit instability, to moisture such as humidity in air, etc.

SUMMARY OF THE INVENTION

The present invention provides a steam sensitive composition and sterilization indicator composition having the following desirable characteristics.

1) The composition exhibits a remarkable color change only when all of the conditions for steam sterilization, i.e. time, temperature and steam have been satisfied.
2) The has good storage stability. Specifically, the steam sensitive compositions do not react at low temperature (e.g. room temperature); are insoluble in and nonreactive with water; and are not sublimable.
3) The composition exhibits a color change after steam sterilization which is uniform and distinguishable.
4) The composition is odorless.

The present invention provides a steam sensitive composition which comprises the combination of a metal complex and an exchange ligand. The metal complex is bis(dimethylglyoximato)nickel [hereinafter referred to as Ni(dmg)$_2$], bis(2-furyldioximato)nickel [hereinafter referred to as Ni(fdo)$_2$], zirconium chloranilate or bis(nioximato)nickel [hereinafter referred to as Ni(nox)$_2$]; and the exchange ligand is either 1) an aminocarboxylic acid which comprises from 1 to 6 carboxylic acid groups and from 1 to 4 amino groups, and its salts; or 2) citric or tartaric acids and their salts.

Still further, the present invention provides sterilization indicator compositions containing as main components the steam sensitive composition described above, a binder, a solvent and preferably a color-change rate regulating component. The rate regulating components may be a cyanate or thiocyanate salt, and/or tartaric or citrate acid and their salts.

DETAILED DESCRIPTION OF THE INVENTION

The present invention utilizes a ligand-displacement reaction which proceeds only under steam sterilization steam conditions, and is represented by the general formula,

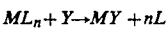

$$ML_n + Y \rightarrow MY + nL$$

wherein ML$_n$ represents a metal complex, Y represents an exchange ligand, M represents a metal, L represents a ligand contributed by the metal complex and n represents a whole number, which in the case of the metal complexes described above, is 2. ML$_n$ is normally a colored metal complex, while Y is normally a colorless exchange ligand. Under steam sterilization conditions ML$_n$ and Y react to produce another metal complex MY and a ligand L, which are colorless or are colored a different color than ML$_n$.

The exchange ligand according to the present invention is either 1) an aminocarboxylic acid which comprises from 1 to 6 carboxylic acid groups and from 1 to 4 amino groups, and its salts; or 2) citric or tartaric acid and their salts. Preferred salts of these acids are the sodium, potassium, calcium and ammonium salts. Particularly preferred examples of the aminocarboxylic acid include ethylenediaminetetraacetic acid [hereinafter referred to as EDTA] and its salt, glycoletherdiaminetetraacetic acid [hereinafter referred to as GEDTA], trans-1,2-cyclohexanediaminetetraacetic acid [hereinafter referred to as CyDTA], nitrilotriacetic acid [hereinafter referred to as NTA] and its salt, iminodiacetic acid [hereinafter referred to as IDA] and its salt, dihydroxyethylglycine [hereinafter referred to as DHEG], N-hydroxyethylenediaminetetraacetic acid [hereinafter referred to as EDTA-OH], hydroxyethyliminodiacetic acid [hereinafter referred to as HIDA], ethylenediaminedipropionic acid dihydrochloride [hereinafter referred to as EDDP], diethylenetriaminepentaacetic acid [hereinafter referred to as DTPA], triethylenetetraminehexaacetic acid [hereinafter referred to as TTHA], 1,3-diaminopropane-2-ol-tetraacetic acid [hereinafter referred to as DPTA-OH] and 1,2-diaminopropanetetraacetic acid [hereinafter referred to as Methyl-EDTA].

A particularly preferred example of a salt of citric acid is diammonium hydrogencitrate. Ammonium tartrate is a particularly preferred tartaric acid salt.

As to the blending ratio of the metal complex to the exchange ligand, the amount of the latter needs to be equimolar or more based on the former in terms of the rate of color change. However, said amount is preferably from 2 to 20 times by mole, most preferably from 2 to 10 times by mole.

The sterilization indicator composition of the present invention having all the foregoing performances contains as essential components the steam sensitive composition of the present invention ($ML_n$ and Y), a binder, and a solvent.

For the binder contained in the sterilization indicator composition of the present invention, any of the general-purpose resins used in ink compositions such as cellulose resins, petroleum resins, phenol resins, maleic acid resins, vinyl resins, etc. may be used. Particularly, nitrocellulose, ethyl cellulose, chlorinated rubbers and chlorinated polyolefins are preferably used. This binder is used to provide sterilization indicators with film-forming properties, good adhesion to objects, heat and moisture resistance, and solubility in drying solvents, particularly in quick drying solvents. Any of the general-purpose solvents used in oil-based inks may be utilized as the solvent in the indicator compositions of the present invention. Useful solvents include alcohols, esters, aromatic hydrocarbons and ketones. Particularly, n-propyl acetate, n-propanol, methanol, 2-ethoxyethanol, butyl acetate, n-butanol, toluene, cyclohexanone and mixtures thereof are preferably used.

In a preferred embodiment of the indicator composition of the present invention, a color-change rate regulating agent is included. Rate regulating agents are preferably either thiocyanate salts, which accelerate the ligand-displacement reaction rate, or cyanate salts which retard the ligand-displacement reaction rate. Preferred cyanate salts include sodium cyanate and potassium cyanate. Particularly preferred are the thiocyanate salts, including ammonium thiocyanate, sodium thiocyanate, potassium thiocyanate and calcium thiocyanate, since they act to speed-up the color forming reaction. Additionally, citric or tartaric acid and their salts can be used as rate regulating agents to speed-up the color forming ability of inks containing other aminocarboxylic acid type exchange ligands.

To the sterilization indicator composition of the present invention may be added substances such as drying oils, semi-drying oils, plasticizers, extenders, dispersing agents, etc. which are usually added to ink compositions for various purposes. The extenders preferably include pigments, for example titanium dioxide, or other commercially available colored pigments commonly used in inks, e.g. "Resino Yellow MD-556-AD", "Resino Blue MD-1132-AD" and "Resino Green MD-2811-AD", all commercially available from Resino Color Industry Co. Ltd., Tokyo, Japan. These pigments exhibit a remarkable effect when a color change different from the inherent one of the steam sensitive composition of the present invention is desired. For example when "Resino Yellow" is added to an indicator composition containing $Ni(dmg)_2$ and EDTA 2Na, an initially red composition turns yellow after exposure to steam sterilization. When "Resino Yellow", the initially brown composition turns green after exposure to steam sterilization.

The sterilization indicator composition of the present invention may be added to various inks such as gravure inks, letter-press inks, screen process inks, stamp inks, etc. By coating this mixture of indicator and ink compositions onto various substrates by the usual coating operations, various tape-form, label-form and card-form sterilization monitoring articles, etc. can be obtained. These articles can also be coated with an adhesive for adhering them to various substrates.

The weight ratio of the essential components is the sterilization indicator compositions of the present invention is preferably as follows: In the case of gravure inks, the preferred ranges of the weights of the steam sensitive composition of the present invention, the binder and the solvent are from 30% to 40% by weight, from 30% to 60% by weight and from 10% to 40% by wight, respectively of the total composition; and in the case of screen process inks, preferred ranges of the weights of the steam sensitive composition of the present invention, the binder and the solvent are from 7% to 33% by weight, from 35% to 65.6% by weight and from 15% to 35% by weight, respectively, of the total composition. As described above, the rate of color change of the composition of the present invention can be altered as desired by changing the blending ratio of the metal complex to the exchange ligand. The rate of color change can also be regulated as desired by adding a color-change rate regulating agent of from 0.1% to 15% by weight, preferably from 1 to 5 percent by weight of the total composition. When the extender is pigment, they can be used to provide a remarkable color change in an amount of from 10% to 100% by weight based on the metal complex. When the extender is titanium dioxide it can be used in an amount of from 50% to 300% by weight based on the same.

Among the compositions of the present invention, by selecting a plural number of compositions differing in color-change conditions from one another and coating them onto the same substrate, a wide variety of practical sterilization indicators can be obtained.

EXAMPLE 1

A mixture of the following components was uniformly ball-milled to prepare the composition of the present invention:

| Components | Amount (part by weight) | Molar Ratio |
|---|---|---|
| $Ni(dmg)_2$ | 1.50 | 1 |
| EDTA.2Na | 15.46 | 8 |
| Binder (nitrocellulose: ethylcellulose = 1:1) | 60.00 | |
| Solvent (n-propyl acetate: n-propanol = 6:4) | 25.00 | |

This composition was coated onto a latex impregnated paper commercially available as "Crepe Paper Backing S-03" from Kojin Co. Ltd., Tokyo, Japan, by means of a Meyer bar (#20) and dried to prepare a test indicator. The color change of this test indicator under conditions of 121° C. for 1 min, 132° C. for 3 min and 132° C. for 15 min in an autoclave are shown in Table 1. The color change was obtained by measuring color difference, $\Delta E$, defined by the following equation using the SZ-Σ80 COLOR MEASURING SYSTEM produced by Nippon Denshoku Kogyo Co., Ltd., incorporated herein by reference:

$$\Delta E = \sqrt{(L - L')^2 + (a - a')^2 + (b - b')^2}$$

wherein L, a and b represent value, hue and chroma, respectively, before color development, and L', a' and b' represent value, hue and chroma, respectively, after color change in the autoclave.

TABLE 1

| ΔE Before Color Development | ΔE After Color Development in Autoclave | | |
|---|---|---|---|
| | 121° C./1 min | 132° C./3 min | 132° C./15 min |
| 0 | 3.26 | 14.40 | 33.39 |

EXAMPLES 2 to 47

Indicators were prepared in the same manner as described in Example 1 using various combinations of metal complexes and exchange ligands, the former to latter molar ratio being 1 to 8, and the same binder and solvent in the same proportion as in Example 1. The color change after exposure in an autoclave was measured by the same method as in Example 1. The results are shown in Tables 2 to 5.

It was found that when the metal complex is $Ni(dmg)_2$ Table 2), the color change of this system upon exposure to steam sterilization is dark red→colorless; when the metal complex is $Ni(fdo)_2$ Table 3), the color change is brown→colorless; when the metal complex is zirconium chloranilate (Table 4), the color change is gray→purple; and when the metal complex is $Ni(nox)_2$ (Table 5), the color change is pale red→colorless.

Compositions having a percent color change of less than 50% when exposed in an autoclave at 132° C. for 15 min react too slowly to be of practical use. However, compositions having a percent color change of 50% or more when exposed in an autoclave at 121° C. for 1 min, change color too quickly to confirm whether or not a definite period of time necessary for steam sterilization has passed. Consequently, such compositions are not suitable in the practice of the present invention. As is apparent from Tables 2 to 5, the compositions of the present invention exhibit the desired color change rates.

TABLE 2

| | | [Metal Complex: $Ni(dmg)_2$] | | | |
|---|---|---|---|---|---|
| Example No. | Exchange ligand (Y) | ΔE Before Color Development | ΔE After Color Development in Autoclave | | |
| | | | 121° C./1 min | 132° C./3 min | 132° C./15 min |
| 2 | EDTA | 0 | 14.33 | 29.37 | 33.36 |
| 3 | EDTA.3Na | 0 | 1.32 | 3.12 | 19.75 |
| 4 | EDTA.2K | 0 | 5.33 | 29.95 | 33.24 |
| 5 | EDTA.3K | 0 | 1.66 | 3.89 | 21.55 |
| 6 | EDTA.2NH₄ | 0 | 8.59 | 19.94 | 32.20 |
| 7 | GEDTA | 0 | 6.01 | 16.50 | 35.34 |
| 8 | CyDTA | 0 | 15.51 | 29.91 | 32.52 |
| 9 | NTA | 0 | 15.34 | 32.28 | 34.66 |
| 10 | NTA.2Na | 0 | 2.21 | 7.48 | 32.45 |
| 11 | IDA | 0 | 9.58 | 27.43 | 32.70 |
| 12 | IDA.2Na | 0 | 3.98 | 12.12 | 25.30 |
| 13 | DHEG | 0 | 7.60 | 18.31 | 28.41 |
| 14 | EDTA-OH | 0 | 13.06 | 27.10 | 33.98 |
| 15 | HIDA | 0 | 13.68 | 30.10 | 30.58 |
| 16 | EDDP | 0 | 2.58 | 6.30 | 17.12 |

Note: Assuming that when ΔE is 33.0, the percent color change is 100%, and when ΔE is 16.5, the percent color change is 50%.

TABLE 3

| | | [Metal Complex: $Ni(fdo)_2$] | | | |
|---|---|---|---|---|---|
| Example No. | Exchange ligand (Y) | ΔE Before Color Development | ΔE After Color Development in Autoclave | | |
| | | | 121° C./1 min | 132° C./3 min | 132° C./15 min |
| 17 | EDTA | 0 | 2.89 | 19.27 | 39.13 |
| 18 | EDTA.2K | 0 | 1.48 | 2.47 | 20.07 |
| 19 | EDTA.2NH₄ | 0 | 1.93 | 8.58 | 35.53 |
| 20 | DTPA | 0 | 7.75 | 38.84 | 39.18 |
| 21 | GEDTA | 0 | 3.96 | 17.80 | 41.67 |
| 22 | TTHA | 0 | 6.35 | 39.07 | 38.49 |
| 23 | NTA | 0 | 14.18 | 36.94 | 44.68 |
| 24 | IDA | 0 | 6.22 | 21.93 | 38.47 |
| 25 | IDA.2Na | 0 | 3.70 | 5.95 | 17.99 |
| 26 | DHEG | 0 | 7.22 | 18.36 | 24.84 |
| 27 | EDTA-OH | 0 | 18.47 | 36.20 | 38.82 |
| 28 | DPTA-OH | 0 | 14.97 | 41.51 | 44.14 |
| 29 | Methyl-EDTA | 0 | 3.68 | 22.74 | 37.61 |
| 30 | HIDA | 0 | 6.23 | 29.13 | 39.57 |

Note: Assuming that when ΔE is 40.0, the percent color change is 100%, and when ΔE is 20.0, the percent color change is 50%.

TABLE 4

| | | (Metal Complex: zirconium chloranilate) | | | |
|---|---|---|---|---|---|
| Example No. | Exchange ligand (Y) | ΔE Before Color Development | ΔE After Color Development in Autoclave | | |
| | | | 121° C./1 min | 132° C./3 min | 132° C./15 min |
| 31 | EDTA | 0 | 1.89 | 4.31 | 11.32 |

TABLE 4-continued (Metal Complex: zirconium chloranilate)

| Example No. | Exchange ligand (Y) | ΔE Before Color Development | ΔE After Color Development in Autoclave | | |
|---|---|---|---|---|---|
| | | | 121° C./1 min | 132° C./3 min | 132° C./15 min |
| 32 | EDTA.2Na | 0 | 4.41 | 12.75 | 16.62 |
| 33 | EDTA.3Na | 0 | 3.01 | 6.99 | 13.54 |
| 34 | EDTA.4Na | 0 | 3.90 | 5.74 | 12.44 |
| 35 | EDTA.2K | 0 | 9.95 | 13.87 | 16.63 |
| 36 | EDTA.3K | 0 | 5.66 | 7.10 | 12.35 |
| 37 | EDTA.2NH$_4$ | 0 | 6.75 | 11.33 | 14.90 |
| 38 | DTPA | 0 | 0.96 | 4.71 | 13.40 |
| 39 | TTHA | 0 | 0.68 | 3.35 | 11.43 |
| 40 | NTA | 0 | 2.61 | 6.71 | 10.39 |
| 41 | NTA.2Na | 0 | 2.30 | 6.69 | 13.23 |

Note: Assuming that when ΔE is 20.0, the percent color change is 100%, and when ΔE is 10.0, the percent color change is 50%.

TABLE 5

[Metal Complex: Ni(nox)$_2$]

| Example No. | Exchange ligand (Y) | ΔE Before Color Development | ΔE After Color Development in Autoclave | | |
|---|---|---|---|---|---|
| | | | 121° C./1 min | 132° C./3 min | 132° C./15 min |
| 42 | EDTA | 0 | 1.08 | 3.69 | 32.36 |
| 43 | EDTA.2NH$_4$ | 0 | 4.29 | 8.03 | 23.68 |
| 44 | DTPA | 0 | 2.18 | 9.61 | 25.84 |
| 45 | TTHA | 0 | 2.64 | 9.67 | 29.49 |
| 46 | EDTA-OH | 0 | 2.91 | 7.60 | 20.12 |
| 47 | DPTA-OH | 0 | 3.96 | 11.01 | 23.48 |

Note: Assuming that when ΔE is 35.0, the percent color change is 100%, and when ΔE is 17.5, the percent color change is 50%.

EXAMPLE 48

A mixture of the following components was uniformly ball-milled to prepare the indicator composition of the present invention:

| Composition | Amount (parts by weight) |
|---|---|
| Ni(dmg)$_2$ | 1.50 |
| EDTA 2Na | 15.46 |
| | [8 times by mole based on Ni(dmg)$_2$] |
| TiO$_2$ | 3.75 |
| NH$_4$SCN | 0.31 |
| Binder: | |
| Nitrocellulose | 5.04 |
| Ethyl cellulose | 5.88 |
| Dibutyl phthalate | 2.52 |
| Methanol | 10.44 |
| 2-Ethoxyethanol | 18.12 |
| n-Propyl acetate | 18.00 |
| Solvent: | |
| n-Propyl acetate | 15.00 |
| n-Propanol | 10.00 |

This composition was coated onto the latex-impregnated paper described in Example 1 by means of a #20 Meyer bar and dried to prepare a test indicator.

The indicator thus prepared turned from pinkish red to white in from 15 to 20 minutes when subjected to steam sterilization at 120° C. and in 3 to 5 minutes at 135° C.

EXAMPLE 49

An indicator was prepared by the same method, and using the same composition described in Example 48, except that ammonium thiocyanate was omitted. The indicator turned from pinkish red to white in 20 to 30 minutes when subjected to steam sterilization at 120° C., and in 5 to 8 minutes at 135° C. Thus, it appears that the addition of ammonium thiocyanate increases the rate of the ligand displacement reaction.

EXAMPLE 50

An indicator was prepared using the same method and composition described in Example 49 except that the amount of EDTA.2Na used was 3.87 parts by weight which is times by mole based on Ni(dmg)$_2$. The indicator turned from pinkish red to white in 8 to 10 minutes when subjected to steam sterilization at 135° C.

EXAMPLE 51

A mixture of the following components was uniformly ball-milled to prepare an indicator composition:

| Composition | Amount (parts by weight) |
|---|---|
| Ni(fdo)$_2$ | 1.5 |
| EDTA 2Na | 7.06 |
| | [8 times by mole based on Ni(fdo)$_2$] |
| TiO$_2$ | 0.75 |
| Chlorinated rubber (as binder) | 24.00 |
| Toluene (as solvent) | 36.00 |

This composition was coated onto latex-impregnated paper and dried to prepare an indicator, as described in Example 1. The indicator turned from brown to white in 20 minutes when subjected to steam sterilization at 120° C., and in 5 minutes at 135° C.

EXAMPLE 52

A mixture of the following components was uniformly ball-milled to prepare an ink composition:

| Composition | Amount (parts by weight) |
|---|---|
| Zirconium chloranilate | 1.5 |

| Composition | Amount (parts by weight) |
| --- | --- |
| NTA | 4.52 (8 times by mole based on zirconium chloranilate) |
| TiO$_2$ | 0.75 |
| Chlorinated polyethylene (as binder) | 12.00 |
| Toluene (as solvent) | 48.00 |

The composition was coated onto latex-impregnated paper and dried to prepare an indicator, as described in Example 1. The indicator prepared turned from gray to violet in 30 minutes when subjected to steam sterilization at 135° C.

EXAMPLE 53

A mixture of the following composition was uniformly ball-milled to prepare an indicator composition:

| Composition | Amount (parts by weight) |
| --- | --- |
| Ni(nox)$_2$ | 1.50 |
| DTPA | 13.84 [8 times by mole based on Ni(nox)$_2$] |
| TiO$_2$ | 1.00 |
| Binder: | |
| Nitrocellulose | 5.04 |
| Ethyl cellulose | 5.88 |
| Dibutyl phthalate | 2.52 |
| Methanol | 10.44 |
| 2-Ethoxyethanol | 18.12 |
| n-Butyl acetate | 18.00 |
| Solvent: | |
| n-Butyl acetate | 18.00 |
| n-Butanol | 12.00 |

The composition was coated onto a latex-impregnated paper and dried to prepare a test indicator, as described in Example 1. The indicator prepared turned from pinkish red to white in 20 minutes when subjected to steam sterilization at 135° C.

EXAMPLE 54

A mixture of the following components was uniformly ball-milled:

| Components | Amount (parts by weight) |
| --- | --- |
| Ni(dmg)$_2$ | 3.00 |
| EDTA 2Na | 30.86 |
| Binder | 50.00 |
| Solvent | 16.67 |

The binder consisted of the following composition:

| Component | Amount (parts by weight) |
| --- | --- |
| Nitrocellulose | 4.20 |
| Ethylcellulose | 4.90 |
| Triacetine | 2.11 |
| Methanol | 8.76 |
| 2-Ethoxyethanol | 15.07 |
| n-Propyle acetate | 14.96 |

The solvent consisted of 10.00 parts n-propyl acetate and 6.67 parts n-propanol.

This composition was coated onto a latex impregnated paper commercially available as "Crepe Paper Backing S-03" from Kojin Co. Ltd., Tokyo, Japan, by means of a #7 Meyer bar and dried to prepare a test indicator.

EXAMPLES 55-62

Indicators were prepared in the same manner as Example 54 using Ni(dmg)$_2$ as the metal complex and various other compounds in place of EDTA 2Na. The amount of binder and solvent was as indicated in Example 54. The amount of Ni(mg)$_2$ and additive was as indicated in Table 6. The color change ($\Delta E$) for the indicators prepared according to Examples 54–62 was measured by the same method as in Example 1, under conditions of 121° C. for 1 minute, and 132° C. for 1, 3, 5, 15 and 30 minutes in an autoclave. The results are shown in Table 6.

TABLE 6

| Example No. | Additive | Ni/Additive (mol/mol) | $\Delta Ei^2$ | $\Delta E$ 121° C. 1 min | 132° C. 1 min | 132° C. 3 min | 132° C. 5 min | 132° C. 15 min | 132° C. 30 min |
| --- | --- | --- | --- | --- | --- | --- | --- | --- | --- |
| | control[1] | 1/0 | 0 | 1.82 | 2.04 | 2.36 | 2.01 | 2.34 | 2.07 |
| 54 | EDTA.2Na | 1/8 | 0.55 | 2.16 | 5.30 | 9.24 | 15.55 | 39.51 | 39.15 |
| 55 | NH$_4$SCN | 1/18 | 2.58 | 2.92 | 3.55 | 4.59 | 5.33 | 6.72 | 11.33 |
| 56 | NaSCN | 1/18 | 1.69 | 3.75 | 3.94 | 4.62 | 4.98 | 4.77 | 5.20 |
| 57 | KSCN | 1/18 | 0.36 | 2.22 | 2.15 | 2.26 | 2.84 | 2.90 | 3.05 |
| 58 | Ca(SCN)$_2$ | 1/9 | 3.09 | 2.02 | 2.36 | 1.74 | 2.55 | 2.92 | 4.14 |
| 59 | NaOCN | 1/18 | 1.77 | 2.17 | 4.35 | 5.86 | 6.49 | 7.22 | 7.62 |
| 60 | KOCN | 1/18 | 0.15 | 1.83 | 2.83 | 4.39 | 5.38 | 6.89 | 7.50 |
| 61 | CH$_3$COONH$_4$ | 1/18 | 1.74 | 1.17 | 1.33 | 1.48 | 1.62 | 1.73 | 1.74 |
| 62 | (NH$_4$)$_2$HC$_6$H$_5$O$_7$ (di-ammonium hydrogencitrate) | 1/6 | 1.27 | 4.31 | 5.36 | 7.18 | 8.85 | 14.49 | 23.34 |
| 63 | (NH$_4$)$_2$C$_4$H$_4$O$_6$ (ammonium tartrate) | 1/9 | 1.93 | 2.81 | 3.71 | 5.66 | 8.92 | 19.24 | 36.55 |

[1] Control is the Ni(dmg)$_2$ in the solvent and binder but with no exchange ligand or other additive
[2] Initial indicator color change between samnple and control Table 6 indicates that di-ammonium hydrogencitrate and ammonium tartrate act as exchange ligands, with performance characteristics approximately equivalent to EDTA 2Na. The other cyanate and thiocyanate salts and ammonium acetate do not react sufficiently with the metal complex to function as exchange ligands in the practice of the present invention.

EXAMPLES 64-68

Indicators were prepared in the same manner as Example 54, using Ni(dmg)$_2$ as the metal complex and various other compounds in place of EDTA 2Na. The color change ($\Delta E$) was measured by the same method as in Examples 55-62. The results are shown in Table 7.

differences ($\Delta E$) were measured by the same method as in Example 1 under conditions of 121° C. for 1 minute and 132° C. for 1, 3 and 5 minutes. Table 8 reports the results of using 1% by weight of the rate regulating agent and Table 9 reports the results of using 5% by weight of the rate regulating agent.

TABLE 8

| Example No. | Rate Regulating Agent (1 wt %) | $\Delta Ei^2$ | 121° C./ 1 min $\Delta E^3$ | 132° C./ 1 min $\Delta E^3$ | 132° C./ 3 min $\Delta E^3$ | 132° C./ 5 min $\Delta E^3$ | note[4] |
|---|---|---|---|---|---|---|---|
|  | control[1] | 0 | 5.50 | 5.57 | 36.25 | 42.68 | — |
| 69 | NH$_4$SCN | 3.39 | 27.26 | 36.35 | 39.82 | 39.99 | faster |
| 70 | NaSCN | 2.46 | 6.32 | 6.94 | 40.50 | 40.86 | similar to control |
| 71 | KSCN | 1.95 | 7.26 | 11.11 | 40.03 | 41.13 | faster |
| 72 | Ca(SCN)$_2$ | 1.35 | 15.26 | 27.21 | 43.17 | 42.86 | faster |
| 73 | NaOCN | 0.51 | 4.04 | 4.31 | 13.64 | 22.13 | slower |
| 74 | KOCN | 0.91 | 3.68 | 3.69 | 18.85 | 33.42 | slower |
| 75 | CH$_3$COONH$_4$ | 1.84 | 3.83 | 10.57 | 39.89 | 42.07 | similar to control |
| 76 | (NH$_4$)$_2$HC$_6$H$_5$O$_7$ | 1.03 | 24.74 | 39.46 | 42.82 | 42.36 | faster |
| 77 | (NH$_4$)$_2$C$_4$H$_4$O$_6$ | 0.90 | 21.52 | 36.39 | 41.63 | 42.01 | faster |

[1]The control was the composition of Example 54, with Ni(dmg)$_2$ and EDTA 2Na, but no rate regulating agents
[2]Initial indicator color change as compared to control
[3]Color change as compared to Ei after exposure to steam sterilization
[4]Faster or slower color development than control

TABLE 9

| Example No. | Rate Regulating Agent (1 wt %) | $\Delta Ei^2$ | 121° C./ 1 min $\Delta E^3$ | 132° C./ 1 min $\Delta E^3$ | 132° C./ 3 min $\Delta E^3$ | 132° C./ 5 min $\Delta E^3$ | note[4] |
|---|---|---|---|---|---|---|---|
|  | control[1] | 0 | 5.26 | 10.16 | 41.05 | 40.55 | — |
| 78 | NH$_4$SCN | 5.35 | 34.18 | 35.16 | 32.98 | 34.15 | faster |
| 79 | NaSCN | 3.83 | 10.96 | 23.53 | 36.58 | 37.18 | faster |
| 80 | KSCN | 2.00 | 16.06 | 32.67 | 35.82 | 36.12 | faster |
| 81 | Ca(SCN)$_2$ | 2.27 | 34.94 | 37.59 | 35.90 | 36.12 | faster |
| 82 | NaOCN | 0.75 | 2.90 | 3.67 | 6.67 | 9.80 | slower |
| 83 | KOCN | 1.51 | 3.52 | 5.14 | 11.37 | 18.06 | slower |
| 84 | CH$_3$COONH$_4$ | 3.65 | 4.48 | 11.28 | 37.26 | 38.21 | similar to control |
| 85 | (NH$_4$)$_2$HC$_6$H$_5$O$_7$ | 2.37 | 36.60 | 41.78 | 40.76 | 41.12 | faster |
| 86 | (NH$_4$)$_2$C$_4$H$_4$O$_6$ | 1.34 | 30.39 | 38.34 | 36.65 | 38.20 | faster |

[1]The control was the composition of Example 54, with Ni(dmg)$_2$ and EDTA 2Na, but no rate regulating agents
[2]Initial indicator color change as compared to control
[3]Color change as compared to Ei after exposure to steam sterilization
[4]Faster or slower color development than control

TABLE 7

| Example No. | Additive | Ni/Additive (mol/mol) | $\Delta Ei^2$ | 121° C. 1 min $\Delta E$ | 132° C. 1 min $\Delta E$ | 132° C. 3 min $\Delta E$ | 132° C. 5 min $\Delta E$ | 132° C. 15 min $\Delta E$ | 132° C. 30 min $\Delta E$ |
|---|---|---|---|---|---|---|---|---|---|
|  | control[1] | 1/0 | 0 | 2.00 | 2.17 | 2.18 | 2.14 | 2.16 | 2.71 |
| 54 | EDTA.2Na | 1/8 | 0.47 | 2.14 | 4.24 | 14.38 | 21.70 | 39.42 | 38.63 |
| 64 | NH$_4$SCN | 1/18 | 2.70 | 2.57 | 3.08 | 2.90 | 3.43 | 5.40 | 6.28 |
| 65 | (NH$_4$)$_2$HC$_6$H$_5$O$_7$ (di-ammonium hydrogencitrate) | 1/6 | 1.76 | 4.86 | 5.36 | 7.19 | 8.94 | 14.76 | 24.00 |
| 66 | (NH$_4$)$_2$C$_4$H$_4$O$_6$ (ammonium tartrate) | 1/9 | 0.61 | 3.71 | 4.29 | 8.11 | 11.11 | 24.56 | 40.25 |
| 67 | C$_6$H$_8$O$_7$ (citric acid) | 1/6 | 2.96 | 5.09 | 4.40 | 6.24 | 9.32 | 18.16 | 32.36 |
| 68 | C$_4$H$_6$O$_6$ (tartaric acid) | 1/9 | 5.95 | 32.98 | 33.90 | 35.37 | 34.79 | 34.34 | 30.49 |

[1]Control is the Ni(dmg)$_2$ in the solvent and binder but with no exchange ligand or other additive
[2]Initial indicator color change between samnple and control Table 7 indicates that tartaric and citric acid act as exchange ligands, with performance characteristics approximately equivalent to EDTA 2Na.

EXAMPLES 69-86

Indicators were prepared as described in Example 1, using the following indicator compositions, including various color-change rate regulating agents. The color The results reported in Tables 8 and 9 illustrate that the thiocyanate, tartrate and citrate rate regulating agents accelerate the speed of the color-producing reaction, while the cyanate rate regulating agents decelerate the color-producing reaction of the indicator compositions of the present invention.

EXAMPLE 87

A mixture of the following components was uniformly ball-milled to prepare an indicator composition:

| Components | Amount (parts by weight) |
| --- | --- |
| Ni(dmg)$_2$ | 3.44 |
| EDTA 2Na | 26.58 |
| TiO$_2$ | 1.72 |
| Ca(SCN)$_2$ | 0.22 |
| green pigment[1] | 1.37 |
| Binder[2] | 50.00 |
| Solvent[3] | 16.67 |

[1] "Resino Green MD-2811-AD", commercially available from Resino Color Industry Co. Ltd., Tokyo, Japan
[2] The binder consisted of the following composition:

| Component | Amount (parts by weight) |
| --- | --- |
| Nitrocellulose | 4.20 |
| Ethylcellulose | 4.90 |
| Triacetine | 2.11 |
| Methanol | 8.76 |
| 2-Ethoxyethanol | 15.07 |
| n-Propyle acetate | 14.96 |

[3] The solvent consisted of 10.00 parts n-propyl acetate and 6.67 parts n-propanol This ink composition was coated onto a latex-impregnated paper dried to prepare a test indicator as described in Example 1. The test indicator thus prepared was brown. It turned completely green in 5 minutes when subjected to steam sterilization at 132° C.

I claim:

1. A steam sensitive composition comprising a metal complex and an exchange ligand, wherein said metal complex is bis(dimethylglyoximato)nickel, bis(2-furyldioximato)nickel, zirconium chloranilate or bis(nioximato)nickel and said exchange ligand is an aminocarboxylic acid which comprises from 1 to 6 carboxylic acid groups and from 1 to 4 amino groups; or citric acid, a salt of citric acid, tartaric acid or a salt of tartaric acid; or a mixture thereof.

2. The steam sensitive composition of claim 1 wherein said exchange ligand is ethylenediaminetetraacetic acid or its salt, glycoletherdiaminetetraacetic acid, trans-1,2-cyclohexanediaminetetraacetic acid, nitrilotriacetic acid or its salt, iminodiacetic acid or its salt, dihydroxyethylglycine, N-hydroxyethylenediaminetetraacetic acid, hydroxyethyliminodiacetic acid, ethylenediaminedipropionic acid dihydrochloride, diethylenetriaminepentaacetic acid, triethylenetetraminehexaacetic acid, 1,3-diaminopropane-2-ol-tetraacetic acid or 1,2-diaminopropanetetraacetic acid.

3. The steam sensitive composition of claim 1 wherein said exchange ligand is diammonium hydrogencitrate or ammonium tartrate.

4. The steam sensitive composition of claim 1 wherein said metal complex and exchange ligand are present in a ratio of 2 to 20 mole exchange ligand per mole of metal complex.

5. A sterilization indicator comprising the steam sensitive composition of claim 1, a binder and a solvent.

6. The indicator of claim 5 wherein said binder is a cellulose resin, a petroleum resin, a phenol resin, a maleic resin, a vinyl resin, a chlorinated rubber or a mixture thereof.

7. The indicator of claim 5 wherein said solvent is an alcohol, an ester, an aromatic hydrocarbon, a ketone, or a mixture thereof.

8. The indicator of claim 5 wherein the indicator composition further comprises a color-change rate regulating agent.

9. The indicator of claim 8 wherein said color-change rate regulating agent is a cyanate salt, a thiocyanate salt, citric acid, a salt of citric acid, tartaric acid, a salt of tartaric acid, or a mixture thereof.

10. The indicator of claim 9 wherein said rate regulating agent is present in a concentration of between about 0.1 and 15 percent by weight of said indicator composition.

11. The indicator of claim 5 wherein the indicator composition further comprises a pigment.

12. The indicator of claim 8 wherein said metal complex is bis(dimethylglyoximato)nickel, said exchange ligand is EDTA 2Na, and said rate regulating agent is ammonium thiocyanate.

* * * * *

UNITED STATES PATENT AND TRADEMARK OFFICE
CERTIFICATE OF CORRECTION

PATENT NO. : 5,064,576
DATED : November 12, 1991
INVENTOR(S) : Kyoko Suto

It is certified that error appears in the above-indentified patent and that said Letters Patent is hereby corrected as shown below:

Col. 4, Line 1, "When 'Resino Yellow' the initially brown composition turns green after exposure to steam sterilization" should read --When "Resino Green" is added to the same composition in place of "Resino Yellow", the initial brown composition turns green after exposure to steam sterilization--.

Col. 10, Line 56, TABLE 6

"example 62,    132°C
                5 min.
                8.85"

should read

--example 62,   132°C
                5 min.
                8.58--

UNITED STATES PATENT AND TRADEMARK OFFICE
CERTIFICATE OF CORRECTION

PATENT NO. : 5,064,576

DATED : November 12, 1991

INVENTOR(S) : Kyoko Suto

It is certified that error appears in the above-indentified patent and that said Letters Patent is hereby corrected as shown below:

Col. 12, TABLE 9 Heading

"Rate Regulating
Agent
(1 wt %)"

should read

--Rate Regulating
  Agent
  (5 wt %)--

Signed and Sealed this

Twenty-fifth Day of October, 1994

Attest:

BRUCE LEHMAN

*Attesting Officer*    *Commissioner of Patents and Trademarks*